(12) United States Patent
Lary et al.

(10) Patent No.: US 7,006,922 B2
(45) Date of Patent: Feb. 28, 2006

(54) STELLAR ICON FOR DATA REPRESENTATION AND SYSTEM AND METHOD FORMING THE STELLAR ICON

(75) Inventors: Todd P. Lary, Homestead, FL (US); John S. Riley, Miami, FL (US); Christopher W. Snow, Homestead, FL (US)

(73) Assignee: Coulter International Corp., Miami, FL (US)

( * ) Notice: Subject to any disclaimer, the term of this patent is extended or adjusted under 35 U.S.C. 154(b) by 280 days.

(21) Appl. No.: 10/139,321

(22) Filed: May 7, 2002

(65) Prior Publication Data

US 2003/0211534 A1 Nov. 13, 2003

(51) Int. Cl.
*G06F 17/00* (2006.01)
*G06F 19/00* (2006.01)
*G06F 7/00* (2006.01)

(52) U.S. Cl. .................... 702/19; 715/762; 715/763; 707/100; 707/104.1

(58) Field of Classification Search ............... 345/837; 702/19
See application file for complete search history.

(56) References Cited

U.S. PATENT DOCUMENTS

| | | | |
|---|---|---|---|
| 5,698,411 A | 12/1997 | Lucas et al. | |
| 5,871,946 A | 2/1999 | Lucas et al. | |
| 6,285,377 B1 | 9/2001 | Greenbaum et al. | |
| 6,459,441 B1 * | 10/2002 | Perroux et al. | 345/837 |
| 6,469,722 B1 * | 10/2002 | Kinoe et al. | 345/837 |
| 6,639,614 B1 * | 10/2003 | Kosslyn et al. | 345/837 |
| 2003/0020762 A1 * | 1/2003 | Budrys et al. | 345/835 |

OTHER PUBLICATIONS

Wikipedia definition for Icon, http://en.wikipedia.org/wiki/Icon_(computing), two pages, accessed May 31, 2005.*
Leary, J.F., et al, "New methods for detection, analysis and isolation of rare cell populations", *SPIE*, vol. 2678, pp. 240-253 (1996).

* cited by examiner

*Primary Examiner*—Marianne P. Allen
(74) *Attorney, Agent, or Firm*—Birch, Stewart, Kolasch & Birch, LLP; Mitchell E. Alter

(57) ABSTRACT

A stellar icon for representing multivariate data includes finger members corresponding to constituents of a sample with a length corresponding to an expression of an attribute of the constituent. The finger members are positioned on the base member so that the finger members corresponding to a constituent with an expression of attribute within a certain range are on the upper portion of the base member, and the finger members corresponding to a constituent with an expression of an attribute that is not in the range are positioned on the lower portion of the base member. A method and system for forming the stellar icon include forming a transformation table including data regarding the range and constituents and attributes to be represented. The transformation table is used to determine the relative position of each finger member on the base member and to determine the length of the finger member so that the length corresponds to the expression of the attribute.

20 Claims, 10 Drawing Sheets

STELLAR ICON FOR DATA REPRESENTATION AND SYSTEM AND METHOD FORMING THE STELLAR ICON

FIELD OF THE INVENTION

The present invention relates to a method and system and an icon for representing data. In particular, the invention includes a method and system for forming an interactive stellar icon to represent sample data corresponding to one or more particular attributes of constituents of a sample.

BACKGROUND OF THE INVENTION

Related Art

Medical research and medical diagnosis often require the analysis of vasts amount of sample data from sample points that are each measured for various constituents. For example, medical research can require profiling of a sample pool of blood samples of numerous individuals participating in a study. This can include determining the activity of enzymes in cells. For example, see Lucas et al. (U.S. Pat. Nos. 5,871,946 and 5,698,411) incorporated herein by reference. Each individual can be considered a constituent of the sample pool and various parameters of the sample of the individual's blood sample can be measured as attributes of the sample. The attributes can be the expressions of elements of the blood such as red blood cells, white bloods, enzyme levels and minerals, etc. Additionally, the attributes can be characteristics of cells such as a count of a particular receptor site on a white blood cell or a certain RNA or DNA sequence.

Another facet of medical research and medical diagnosis includes using tissue or blood samples to diagnose disease and broadly assess the state of a person's health, etc. In this situation, one blood sample can be analyzed for numerous constituents such as various enzymes, white blood cells, red blood cells, nutrient levels, enzyme levels and the various characteristics of the cells, etc. Each constituent can then be characterized based upon its attributes.

To analyze the sample data of both an individual's blood and a pool of samples from numerous individuals, biplots can be used. Biplots provide a two-dimensional graphical display of sample data for multivariate sample data such as a sample pool of blood samples or sample data of the various constituents and attributes of an individual blood sample. FIG. 1 provides an example of a biplot. The biplot for either the individual sample or the sample pool are based on principal component analysis (PCA). For a discussion of PCA, see Leary et al., "New Methods for Detection Analysis and Isolation of Rare Cell Populations," SPIE vol. 2678, pgs. 240–253, 1996, incorporated herein by reference.

FIG. 1 depicts one example of a biplot according to the prior art. The biplot of FIG. 1 represents multivariate data by placing vectors A, B, C, and D in multidimensional space on a principal component plane for the first principal component P1. Each vector A, B, C, and D has a length proportional to the variance of data corresponding to the particular constituent A, B, C, and D or the expression of a particular constituent. The angle between the vectors corresponds to the degree of disparity between the attributes of the vectors A, B, C, and D. For a discussion of biplots, see Leary et al.

FIG. 2 depicts another type of prior art that indicates the presence of three constituents having various percentages of a cell phenotype. The "+" and "−" signs indicate the presence or absence, respectively, of the constituents on a cell. As depicted by FIG. 2, a sample of 8% of the cells contains none of three constituents, and a sample of 12% of the cells is positive for one constituent while the other two constituents are absent.

Other fields of study have similarly complex multivariate data analysis needs. For example, criminal research can require developing a profile of the psychological characteristics of criminals that commit particular crimes. Also, geology can require analyzing the attributes of a myriad of soil and groundwater samples corresponding to many wells or borings in a research site.

Technology is continually advancing and allowing computers and processors to process increasing amounts of complex data. Additionally, it has become possible to use artificial intelligence to determine if data results are favorable or unfavorable. As the ability to analyze vast amounts of data has increased and changed biplots have become insufficient tools for representing data. For example, biplots do not present data in a format that allows a user to readily read and understand the results including unfavorable sample data and/or favorable sample data. Additionally, biplots are limited to a two dimensional representation of the data which can present a distorted view of the angle between the vectors.

Previously, it has been a problem to represent multi-parametric data in a single display whether it is in a two or three-dimensional representation. Another shortcoming of the prior art has been its failure to inform the user of the meaning of the data. The present invention overcomes these and other problems by creating an iconized data display which gives the ability to distill complex data into a quick snapshot image, which reveals unique parameters, associated with clinical relevance.

SUMMARY OF THE INVENTION

One embodiment of the invention includes a method of representing a plurality of constituents of a sample. In the method, at least one constituent is designated as being acceptable or unacceptable as a function of a presence of the constituent or at least one attribute of the constituent. Also, a plurality of finger members are formed such that each finger member of the plurality of finger members corresponds to at least one constituent of the sample and each finger member has a base and a length which are functions of an expression at least one attribute of the corresponding constituent. A base member is also formed such that the base member has a first portion and a second portion. An icon is formed by positioning the base of each finger member corresponding to a constituent designated as acceptable on the first portion of the base member and positioning the base of each finger member corresponding to a constituent designated as unacceptable on the second portion of the base member. The icon is also displayed.

The method may also include analyzing the sample to determine the attributes of a plurality of constituents in the sample and selecting constituents of a plurality of constituents of a sample to be represented.

Constituents and attributes to be represented may also be determined. Data organization and compression may be performed to identify constituents and attributes to be represented based on a degree of variance. Constituents may also be selected based on an importance or expression of each constituent. The importance of each constituent is determined by an evaluation of a database of constituent attributes of a plurality of research samples. Selecting constituents may also include using an artificial intelligence system to select the constituents based on the importance of each constituent as determined by the artificial intelligence system evaluation of a database of research samples.

To designate each selected constituent as being acceptable or unacceptable, a database of constituent attribute data may be formed and a range of expression for each attribute or plurality of attributes is determined by analyzing the constituent attribute data in the database. Also, an attribute expression is determined for each attribute of each constituent of the sample or plurality of attributes of each constituent of the sample. Further, it is determined whether or not each attribute expression is within or equal to the determined range. A constituent is designated as acceptable when the corresponding attribute expression is within the determined range, and unacceptable when the attribute expression is not within the determined range.

The step of designating each constituent as acceptable of unacceptable also may include designating each constituent as being acceptable or unacceptable as a function of the expression a plurality of attributes of the constituent.

The attributes of the constituents may be represented by the finger members. For example, a color or shading may be applied to the finger member such that a different color or shading represents each attribute of the plurality of constituents of the sample. Also an expression of an attribute may be identified by a position of the finger member on the base member including positioning a finger member with the highest expression of an acceptable attribute on a relatively highest position of the first portion of the base member and positioning the finger member with the highest expression of an unacceptable attribute on the relatively lowest point of the second portion of the base member. Additionally, a finger member can represent a plurality of constituents.

The base member is circular, spherical, oval, polygonal or any three dimension configuration. Further, the first portion of the base member is opposite and/or above the second portion.

The represented sample may include a sample such as a blood, chemical or organic tissue sample. Also, the icon may be displayed on a monitor or printed by a printer.

Links between the finger members' and base member's respective data also may be incorporated into the icon. A first link may be incorporated into a finger member such that the link associates the finger member and finger member data corresponding to the constituent and at least one attribute of the finger member. A second link maybe incorporated into the base member such that the link associates the base member and base member data including a patients name or research study. Also, the finger member data or base member data are displayed when a user selects the first or second link, respectively.

A second embodiment of the invention includes a system for generating an icon representing attributes of constituents of a sample including a selector using constituent and attribute sample data to select an icon corresponding to the sample data; a designator designating at least one constituent of the plurality of constituents as being acceptable or unacceptable as a function of a presence of the constituent or at least one attribute of the constituent; and, a processor forming the icon by placing a finger member corresponding to at least one constituent of the plurality of constituents on a base member such that a length of the finger member is a function of an expression of at least one attribute of the corresponding constituent and each finger member corresponding to a constituent or attribute designated as acceptable is oriented on a first portion of the base member and each finger member corresponding to a constituent designated as unacceptable is oriented on a second position of a base member.

The system may also include an analyzer for determining the expression of each constituent of the plurality of constituents of a sample. The sample may be a blood, chemical or tissue sample. Also, the designator may include a transformation table for determining that each finger member corresponding to a constituent designated as acceptable is positioned on the first portion of the base member and each finger member corresponding to a constituent designated as unacceptable is positioned on the second portion of the base member.

A third embodiment of the invention is a method of representing multivariate medical data samples including blood or tissue samples from an individual or a plurality of individuals as an icon. The method includes designating at least one constituent of the medical sample as being acceptable or unacceptable as a function of a presence of the constituent or at least one attribute of the constituent; forming a plurality of finger members such that each finger member of the plurality of finger members corresponds to at least one constituent of the medical sample and each finger member has a base and a length which are functions of an expression at least one of attribute of the corresponding constituent; forming a base member such that the base member has a first portion and a second portion; forming an icon by positioning the base of each finger member corresponding to a constituent designated as acceptable on the first portion of the base member and positioning the base of each finger member corresponding to a constituent designated as unacceptable on the second portion of the base member; and displaying the icon.

A fourth embodiment of the invention includes a system for representing multivariate medical data samples including blood or tissue samples from an individual or a plurality of individuals as an icon. The system includes a selector using constituent and attribute sample data to select an icon corresponding to the sample data; a designator designating at least one constituent as being acceptable or unacceptable as a function of a presence of the constituent or at least one attribute of the constituent; and a processor forming the icon by placing one finger member corresponding to each constituent of the plurality of constituents on a base member such that a length of the finger member is a function of an expression of at least one attribute of the corresponding constituent and each finger member corresponding to a constituent designated as acceptable is oriented on a first portion of the base member and each finger member corresponding to a constituent designated as unacceptable is oriented on a second portion of a base member.

A fifth embodiment of the invention is an icon for representing multi-dimensional medical data from a sample or a plurality of samples of blood or tissue. The icon includes a base member having a first portion and a second portion; a plurality of finger members such that each finger member of the plurality of finger members corresponds to at least one constituent of the medical sample and each finger member has a base and a length which are functions of the presence of at least one attribute of the corresponding constituent; a first link embedded in each finger member, the first link associating the corresponding finger member with names and expressions of the constituent and attribute represented; and a second link embedded in the base member, the second link associating the base member with information about the medical sample, whereby selecting the first link will actuate a processor to display on a monitor the data associated with the represented constituent and attribute, and selecting the second link will actuate the processor to display information about the medical sample on the monitor.

These and other objects of the present invention will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The present invention will become more fully understood from the detailed description given herein below and the accompanying drawings, which are given by way of illustration only and thus, are not limitative of the present invention and wherein.

DETAILED DESCRIPTION OF THE INVENTION

Figure 3:
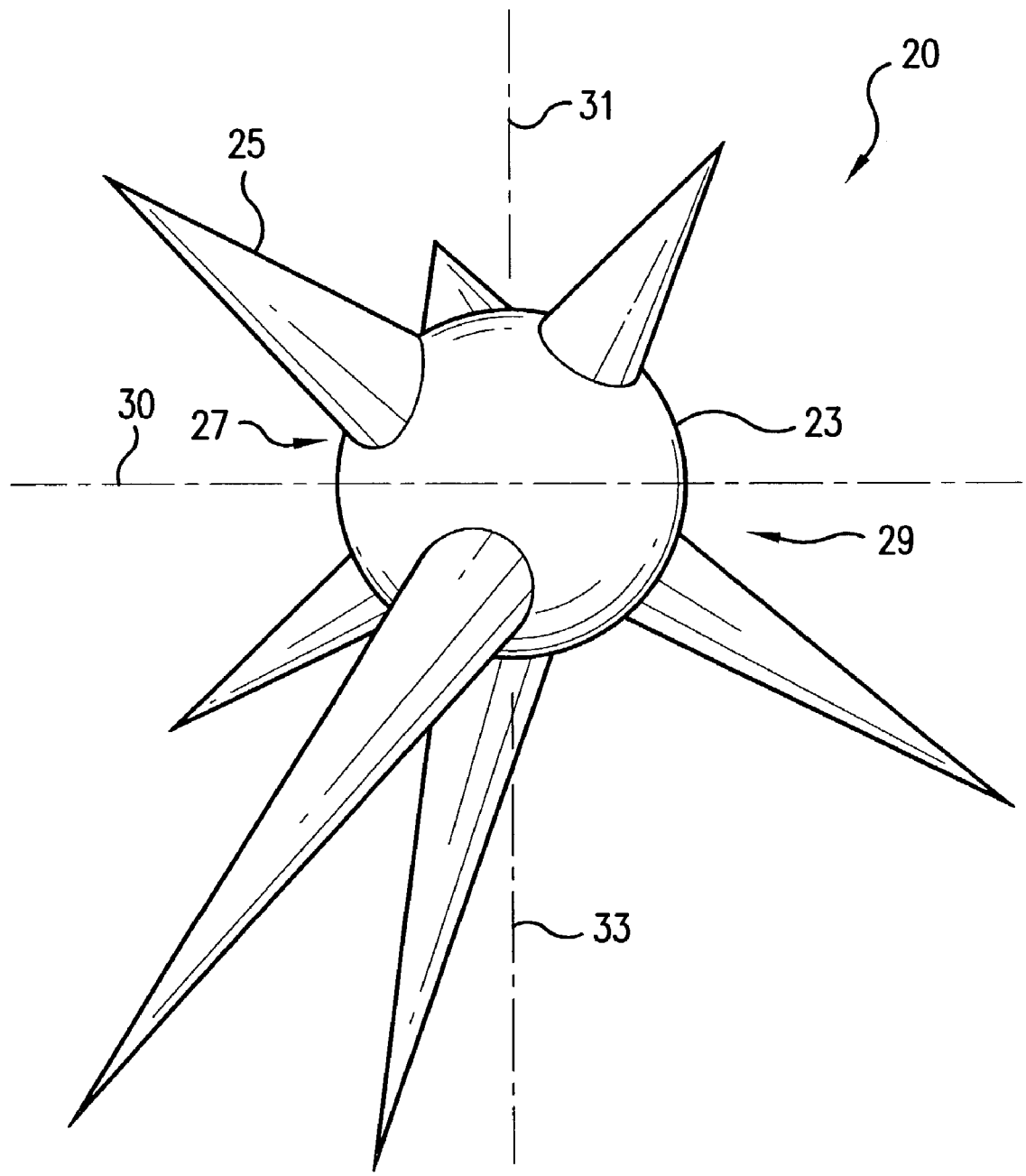
FIG. 3 depicts a stellar icon of the present invention.

As shown in FIG. 3, a stellar icon 20 is formed as a representation of sample data, according to the present invention. The stellar icon 20 is generated based on data processing, as discussed below, and can be output by a computer or other processor on a monitor or printer in a paper form. The icon 20 includes a base member or portion 23, and a plurality of finger members or portions 25.

Although the icon 20 is depicted in two dimensions, it is actually a three dimensional representation of the data which can be limited to two dimensions due to its containment in a two-dimensional medium such as paper. However, the icon 20 can be displayed on a monitor in an interactive mode to permit viewing in three dimensions.

In the preferred embodiment, the base portion is spherical, but shape of the base portion can be any circular, elliptical, polygonal or amorphous three-dimensional shape. As shown, the shape of the finger portions 25, according to a preferred embodiment of the invention, is conical or triangular, however, the finger portions can have other shapes such as rectangular or cylindrical and be of one or more colors.

The base portion 23 has two areas 27 and 29 separated by an imaginary horizontal dividing line 30 onto which the finger portions 25 can be positioned based on (1) whether or not certain attributes or constituents are present in the sample data, (2) whether or not certain attributes or constituents are present in normal or abnormal concentrations or (3) whether or not certain attributes or constituents are present in desirable or undesirable amounts, etc. For example, in the preferred embodiment, the upper portion or hemisphere 27 of the base portion 23 is designated for positive sample data such as sample data that reflects a particular constituent or combination of constituents is present in the data or within a certain range of attributes. The lower portion or hemisphere 29 is designated for data of negative samples or samples that do not contain the measured attribute or constituent or contain the attribute or constituent in a certain range.

Each finger portion 25 represents one or more constituents of a sample or sample pool and corresponds to an expression of an attribute of the represented constituent or constituents. A constituent is a component of a sampled product and may include one or more elements of the sample or the solution to an equation constituting the elements. For example, a single finger portion 25 can correspond to a single constituent measured in an individual's blood, such as Suppressor T-cells or the total T-cells in the sample. Additionally, when samples are taken from a pool of individuals, each finger portion 25 can represent, for example, the presence of a particular constituent within that pool including a different finger portion corresponding to components of blood such as red blood cells, white blood cells, enzymes and nutrients, etc. Alternatively, individuals sampled may be constituents and each finger portion 25 can have a one to one correspondence with each individual sampled so that each finger portion 25 corresponds to the expression of an attribute of a particular constituent of an individual's blood sample. An expression can include, but is not limited to, the statistical properties of an analyzed specimen; for example, it can include the standard deviation of one or more measurements, shape of a component of the test sample, or even counts, percentages and concentrations of either a component of the test sample or an analyte reacted with the test sample, etc.

The finger portions 25 have different aspects, which are useful in representing attributes of constituents, such as the length, thickness, color, shape and position on the base. An attribute is a quality or characteristic of a constituent. The length of a finger portion 25 can vary according to the strength or degree of the presence of a particular attribute of a constituent in a sample or be scaled according to its clinical significance. For example, in a study of a pool of individuals for the presence or expression of a particular cell receptor where each finger portion 25 represents an individual sample, a sample with a higher expression of the receptor site would be represented with a relatively longer finger portion 25 than a sample with a relatively lower expression of the particular cell receptor. The thickness of the finger portion 25 can be relative to the importance or number of constituents that comprise the finger or any predefined attributes of the constituents.

The color of the finger portion 25 can also be used to depict aspects of the sample. For example, the color of each finger portion 25 can be unique so that each constituent of the sample data being measured or studied is represented with a different color. Alternatively, the color of the finger portions could be assigned based on the presence or absence of a particular constituent. For example, if a particular RNA sequence is present in a constituent, the color of the finger portion 25 could be assigned blue and if the RNA is not present then the color could be assigned red. Further, the shading of the colors in either case can be used to represent the expression of an attribute. For example, darker shading could represent a relatively higher expression of the attribute and lighter shading could represent a relatively lower expression of the attribute. Moreover, combination of shading can be employed to depict varying levels of expression within a constituent.

The position of finger portion 25 on the base portion 23 can be based on the properties of the attributes of constituents. According to the preferred embodiment of the invention, the finger portions 25 that represent constituents or attributes that are within a desired range of expression are positioned on the upper hemisphere 27 so they point in an upward direction. Those finger portions 25 that represent constituents or attributes that are not within the desired range of expression are positioned on the lower hemisphere 29 so they point in a downward direction.

Further, the finger portions 25 are positioned on their respective hemisphere 27, 29 based on the relative strength of the expression of the particular constituent or attribute they represent. For example, each hemisphere 27, 29 has a corresponding pole 31 and 33, and a finger portion 25 corresponding to the most desirable expression of an attribute is positioned closest to the upper pole 31 of the base portion 23. Additionally, the finger portions 25 corresponding to the least desirable expression of the attribute is positioned closest to the lower pole 33 of the base portion 23. For example, a desirable expression of the constituent lymphocytic cells would be 30% of white blood cells, which would be positioned at the upper pole 31 of the base portion 23.

The other finger portions 25 which have less extreme properties are positioned in between the dividing line 30 of the base portion 23 and the poles 31, 33 on the appropriate hemisphere 27, 29 based on the relative strength of expression of constituent such that those finger portions with a more desirable or undesirable expressions are positioned closer to the poles 31 and 33 and those with a lower relative strength expression are positioned further from the poles 31 and 33 so that they are closer to the midpoint of the base portion 23.

The designation of the regions of the base portion 23 and positioning the finger portions 25 is not limited to an upper and lower relationship. Other relationships can be useful such as a designation of opposing surfaces of the base portion 23. Additionally, the poles 31 and 33 are not limited to an axis of rotation but may be, for example, the highest or lowest points of the respective portions of a base portion.

Figure 4:
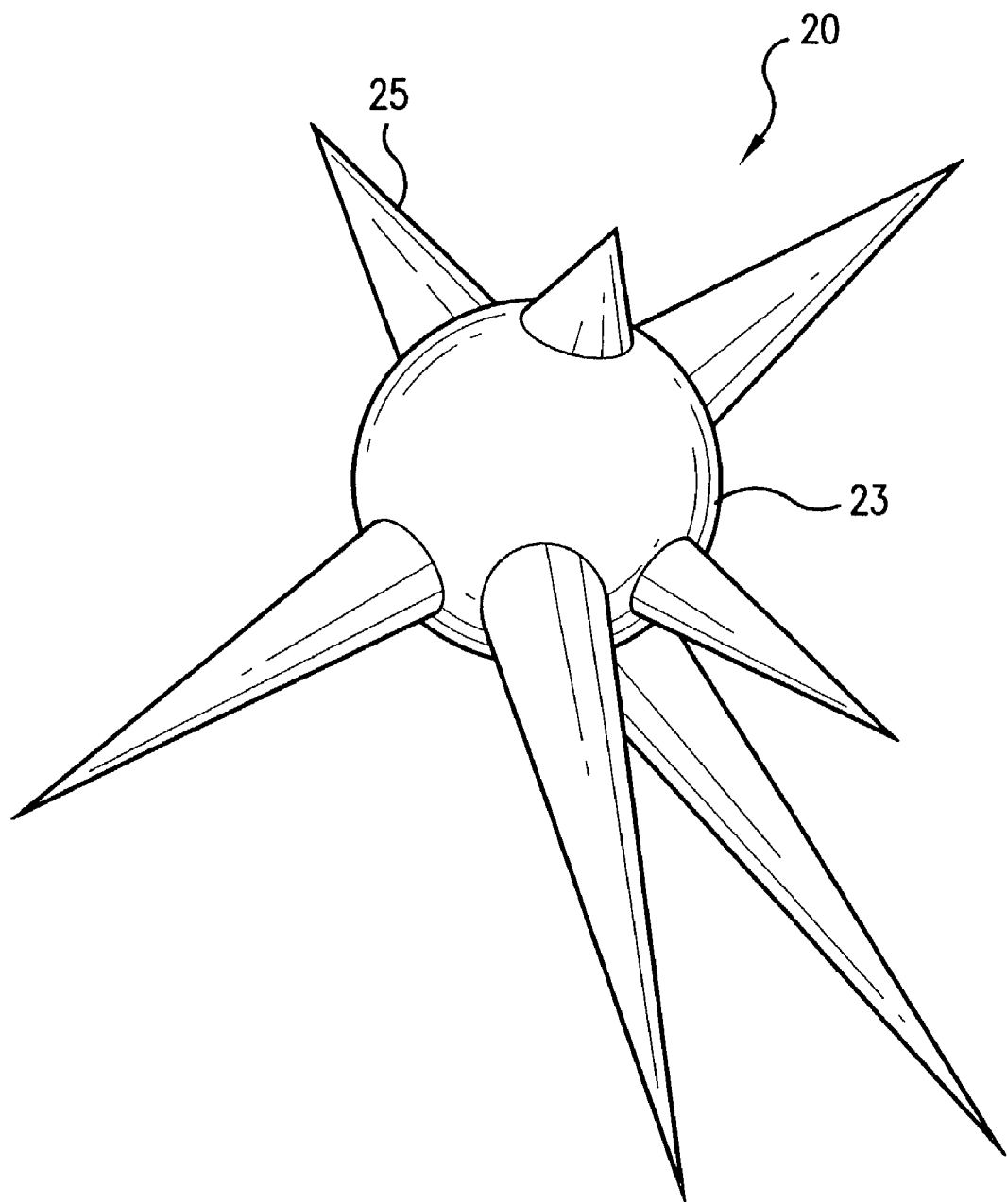
FIG. 4 depicts a rotated view of the stellar icon of FIG. 3.

Once the stellar icon 20 is displayed on a monitor, a user can direct the computer to rotate the stellar icon 20 as shown in FIG. 4 so that the icon 20 can be viewed from a different side. Additionally, a user can direct the computer to generate a print out of a particular view of the icon 20. In this way, the icon 20 can provide three-dimensional representations of the data. Other displays of the icon 20 are envisioned such as a three-dimensional hologram.

Figure 5A:
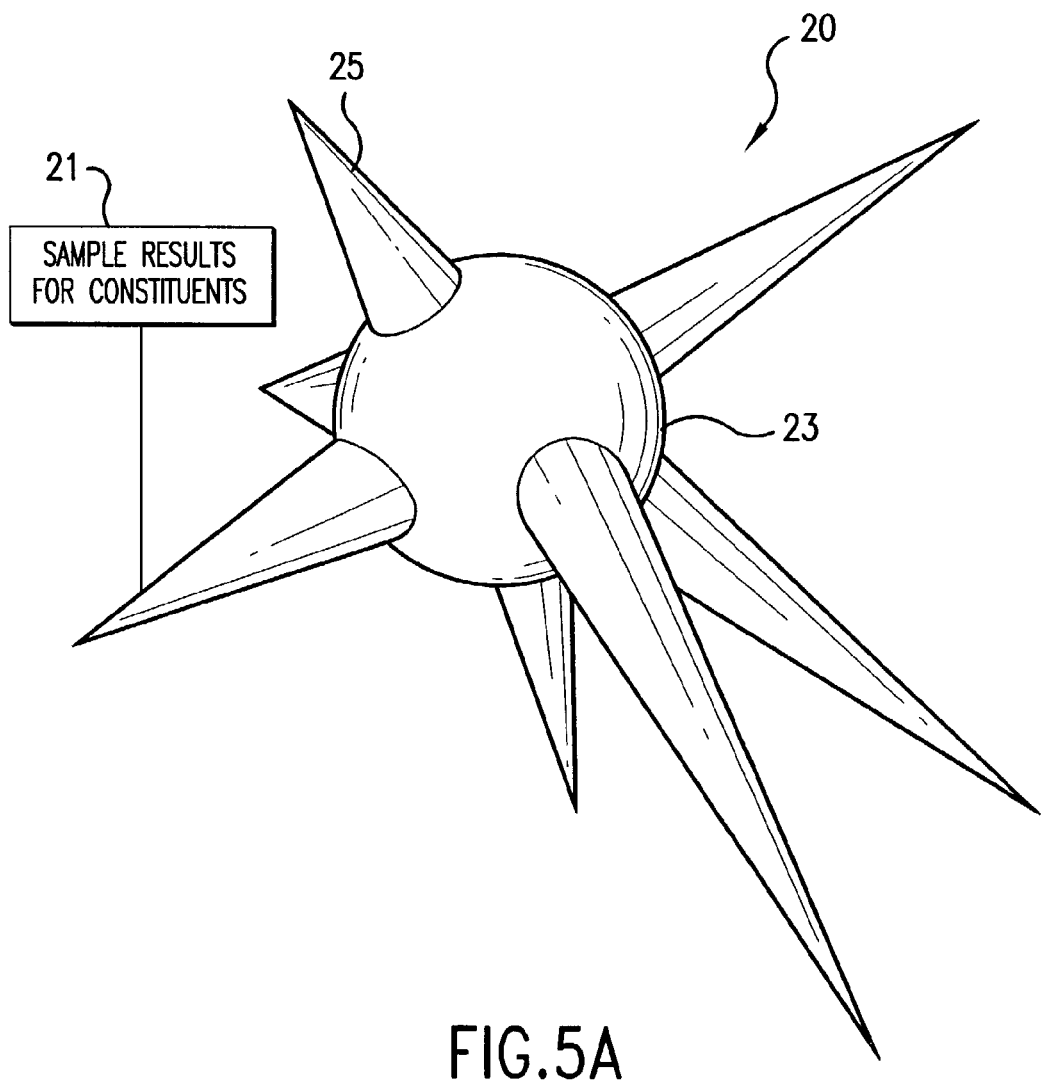
FIGS. 5A and 5B depict the display of the stellar icon of FIG. 3 with the link of the finger portion and the base portion selected, respectively.
Figure 5B:
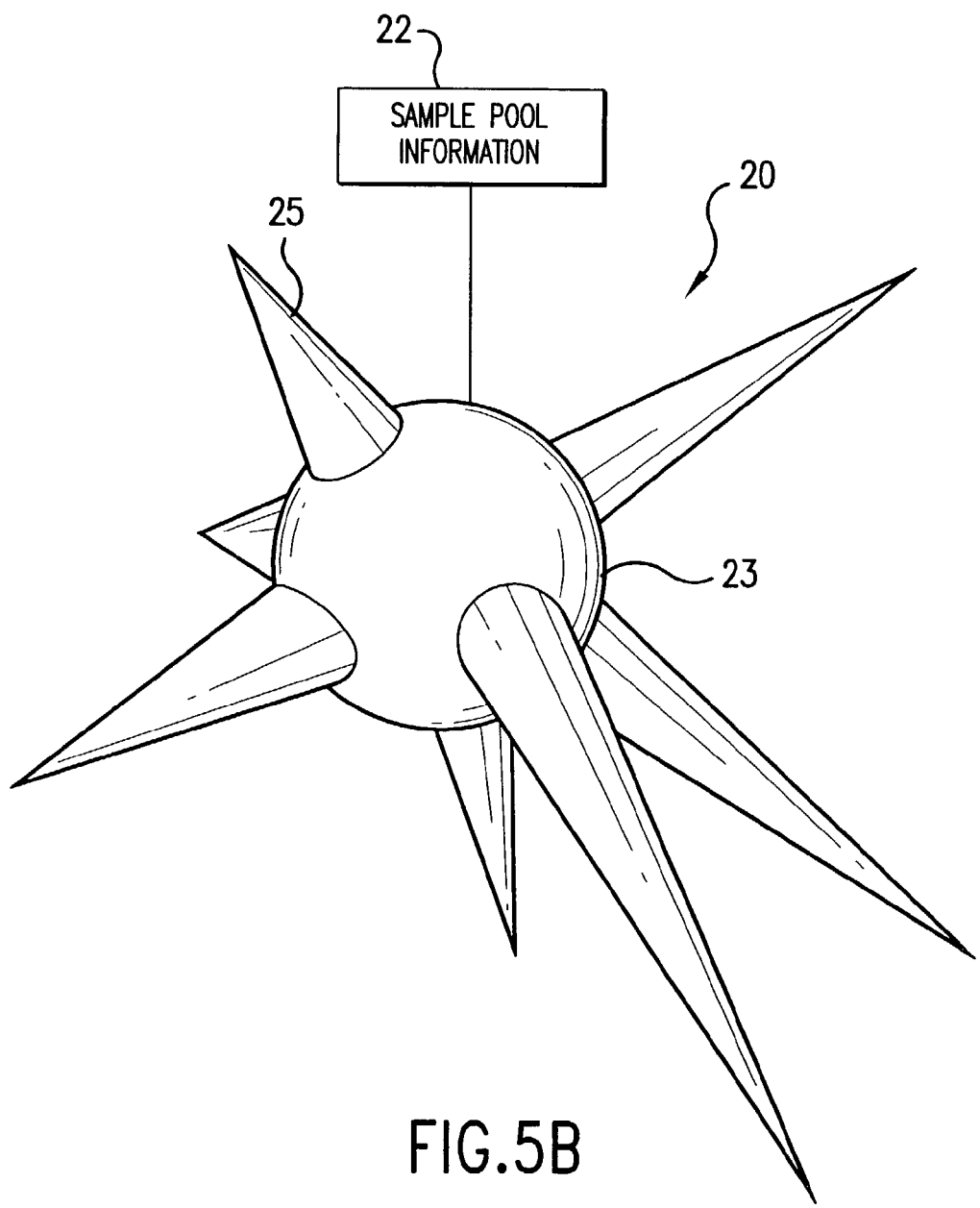
Figure 9:
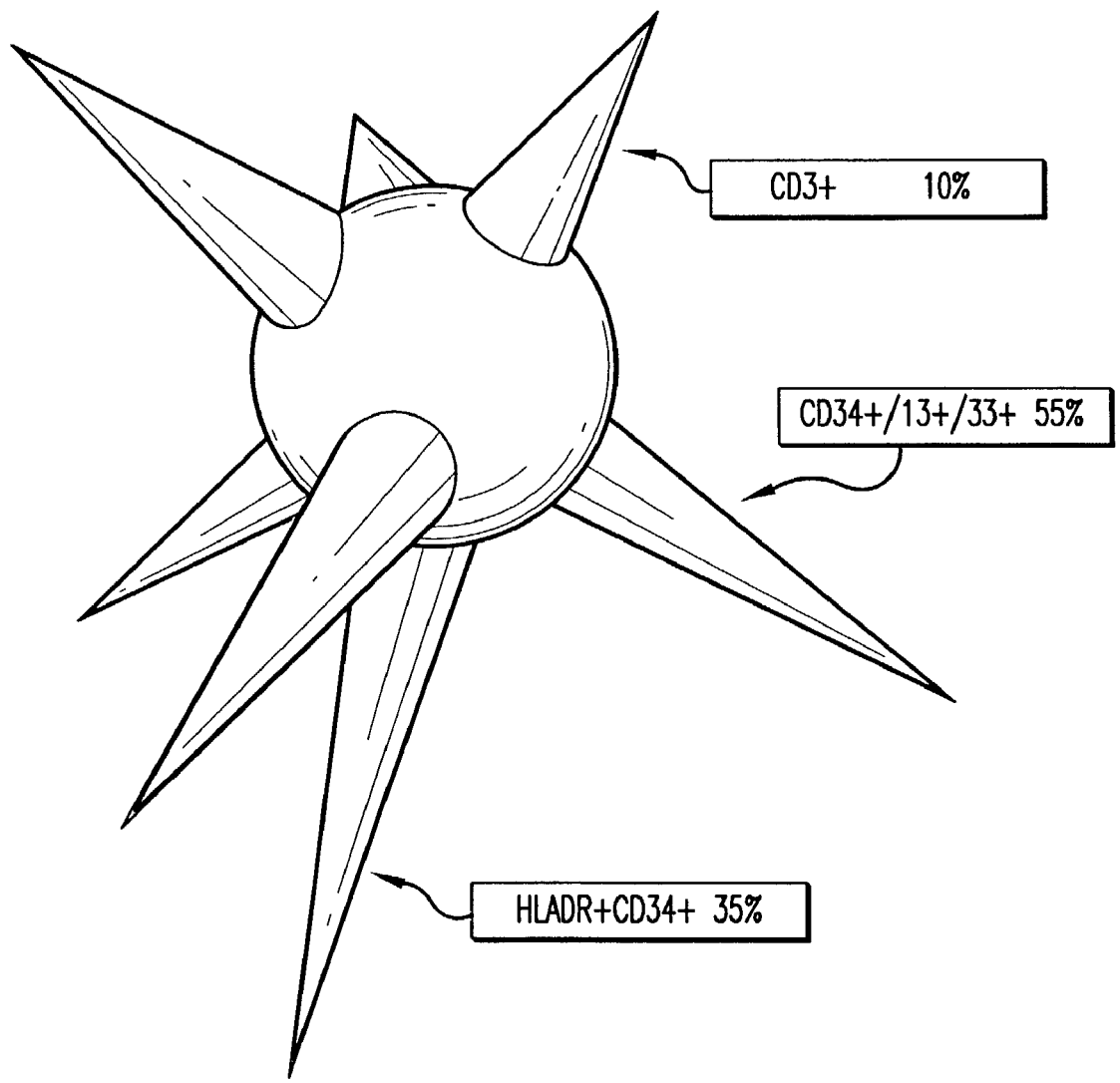
FIG. 9 depicts a stellar icon with an indication of the attributes of three of the depicted constituents.

The icon 20 also contains links to the data that each portion of the icon 20 represents. Object Linking and Embedding (OLE), for example, can be used so that selection of a particular portion of the icon by the user will actuate a processor to also display the raw data associated with that portion or the editable transformation table values of the characteristics of that portion. For example, if a user selects a particular finger portion 25, the monitor can display in window 21 the names of the constituents and attributes that the finger portion represents and the sample data corresponding to the selected finger portion 25, as shown in FIG. 5a. When the user selects the base portion 23, a window 22 can display information about the sample pool and study, as shown in FIG. 5b. In addition, a further graphical representation can be displayed upon selection of a finger portion 25 that will display the combined constituents and attributes used to create the particular finger portion 25, as shown in FIG. 9.

The use of the stellar icon 20 to represent data has many advantages and benefits. First, the stellar icon is capable of being displayed in three dimensions. This allows constituent data to be more spaced apart and easier to interpret. Also, the stellar icon overcomes the distortion, which occurs in a limited two-dimensional display and makes the results easier to read.

Second, the stellar icon 20 also simplifies the interpretation of the data by placing specific constituents on the predetermined areas of the base portion. For example, the upper hemisphere 27 could be designated for favorable results and the lower hemisphere 29 could be designated for unfavorable results. Using these designations, finger portions 25 that represent disease indicating constituents or attributes could be placed on the lower hemisphere 29 and finger portions representing non-disease indicating constituents or attributes could be placed on the upper hemisphere 27. This format allows the user to readily identify those constituents or attributes in the sample that can be problematic. Also, the use of the upper hemisphere 27 and lower hemisphere 29 for displaying favorable and unfavorable results, respectively, is similar to other notions of thoughts such as a "thumbs up" or "thumbs down" for designating favorable and unfavorable.

Third, the stellar icon 20 has many features which can be varied to further indicate the favorable and unfavorable characteristics of a particular constituent or attribute making it versatile to represent multivariate data. These features include, for example, the position of the finger portion on the base portion, the thickness of the finger, the color of the finger portion and the length of the finger portion, and other graphical manipulations of the finger.

Figure 6:
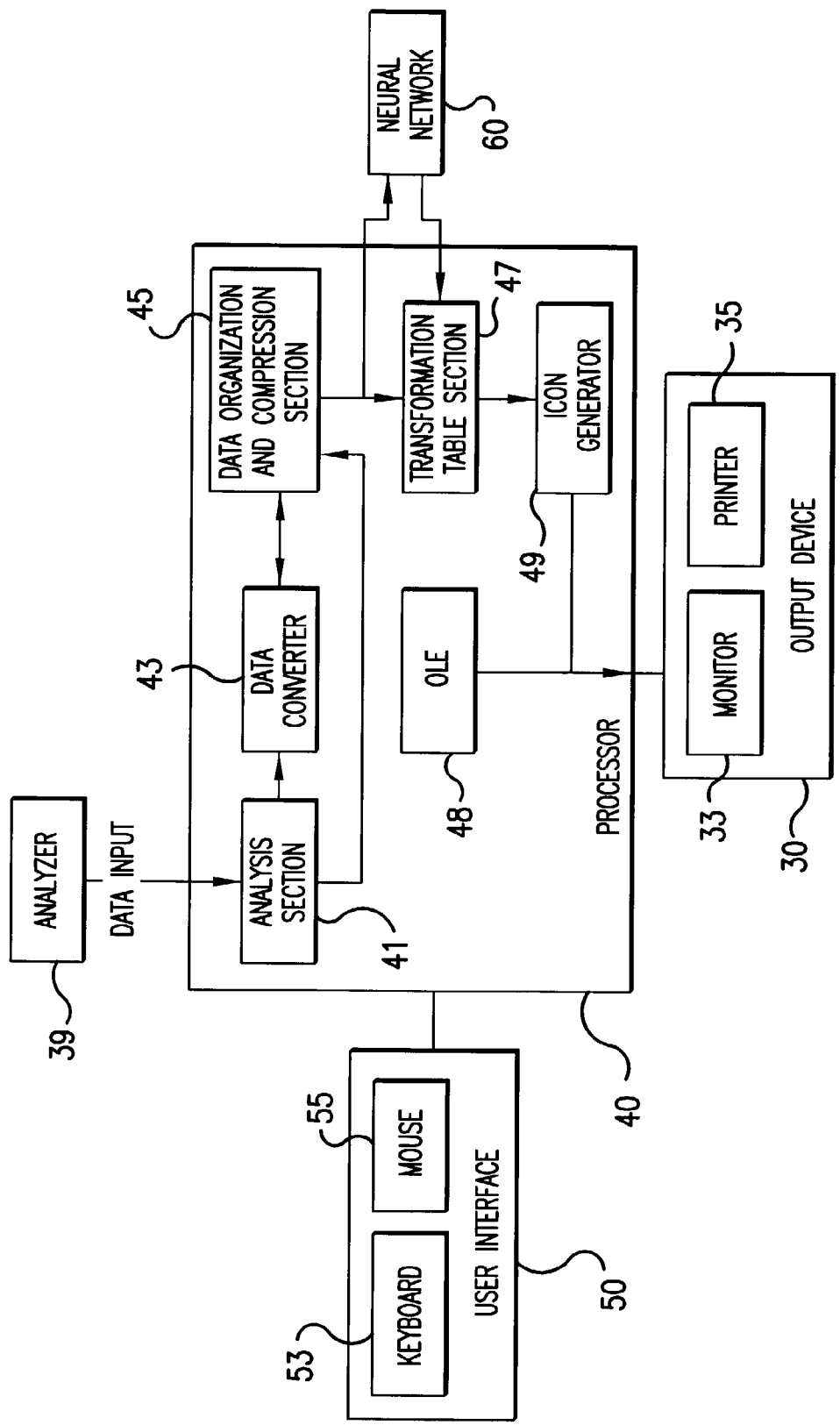
FIG. 6 depicts the preferred embodiment of the system components of the present invention for creating the stellar icon of FIG. 3.

FIG. 6 depicts the preferred embodiment of the system components of the present invention for creating the stellar icon 20. As shown in FIG. 6, the system includes output device 30, a computer or processor 40 having a user interface 50 and an artificial intelligence component, such as a neural network 60. The output device 30, user interface 50 and neural network 60 are in communication with processor 40, which provides a central point of communication between the various devices of the system.

The processor 40 includes an analysis section 41, data converter 43, data organization and compression section 45, transformation table or designator 47, OLE section 48 and an icon generator 49. The analysis section 41 receives input sample data and uses a series of analysis algorithms, such as clustering or gating algorithms, to determine the attributes for one or more predetermined constituents. This procedure can be performed according to unsupervised clustering algorithms, such as K-Means Clustering, Bishop, C. M. "NOVEL NETWORKS FOR PATTERN RECOGNITION", Oxford England: Oxford University Press, 1995; or through pattern recognition techniques, such as described in Gonzales, R., Woods R., "DIGITAL IMAGE PROCESSING," Addison Wesley Publishing Company, Reading, Mass. 1992; or through distance measurements, such as Euclidean distances and Voronoi diagrams, see Reyes C. and Adjouadi, M., "A DIRECTIONAL CLUSTERING TECHNIQUE FOR RANOM DATA CLASSIFICATION" Cytometry 27:126–135, 1997; and artificial analysis techniques, such as in a self organizing maps as taught by Fausett, L., "FUN- DAMENTAL of NEURAL NETWORKS": ARCHITECTURES, ALGORITHMS & APPLICATIONS, Prentice Hall Inc, NJ, 1994. In addition, the data can be manually gated using software.

In the preferred embodiment, the input sample data can be in the form of a spreadsheet or database with a row for each sample and a column for the result of the sampled attribute and/or constituent. The data converter 43 receives the input data from the analysis section 41 and converts the data into an image format (describe below). The data organization and compression section 45 converts the input data from the analysis section 41. The results of the data organization and compression section 45 are provided to the neural network section 60. The transformation table 47 receives information from the neural network, which specifies the icon location in a transformation table, which the transformation table 47 controls. The transformation table 47 then utilizes the results of the data organization and compression section 45 to designate the constituents and their attributes for the icon generation section 49. The icon generator 49 generates the icon 20 according to the instructions provided by the transformation table. The OLE section 48 directs the processor to display the data on the monitor according to the user selections.

The neural network 60 is an artificial intelligence device that can continually learn about the meaning of sampling results and maintain a database of the population data for various constituents and attributes. For example, through the analysis of many samples in a sample pool, the neural network 60 will begin to recognize the trends or the levels of certain attributes.

Then, the neural network 60 can establish rules for analyzing future samples. For example, the neural network can analyze numerous blood samples of normal healthy individuals and determine that a majority of the samples have an expression of a particular receptor site on white cells that is in a range between X and Y. Then, when the neural network 60 receives sample data from an individual with an expression of the same receptor site that exceeds the range, the neural network 60 will recognize this as an abnormal result. Additionally, the neural network 60 can update its stored database and/or rules with the result. Moreover, the neural network 60 can receive user direction from someone such as a doctor, researcher or health care worker or a linked device.

The output device 30 can include a monitor 33 and/or printer 35 and other output devices such as a floppy drive and CD drive for recording of the electronic data. The user interface 50 can include a keyboard 53, mouse 55 or other input device.

The data can be input to the processor 40 from various sources. For example, the data can be received by the processor 40 from communication between the processor 40 and other laboratory equipment, such as analyzer 39 used for actually analyzing the sample data. The processor 40 can also receive the input data by scanning a spreadsheet of the data, copying the data from electronic media, accessing data from the internet, or manual input, etc.

The system of the present invention can be implemented by software programs used by hardware and is not limited to the representation of FIG. 6 and the discussion above. Rather, other configurations are envisioned. For example, the neural network 60 can be replaced with any process that minimizes error of a desired outcome or can be replaced by a measure of similarity. Also, additional processors can be used to perform some functions of processor 40.

Figure 7:
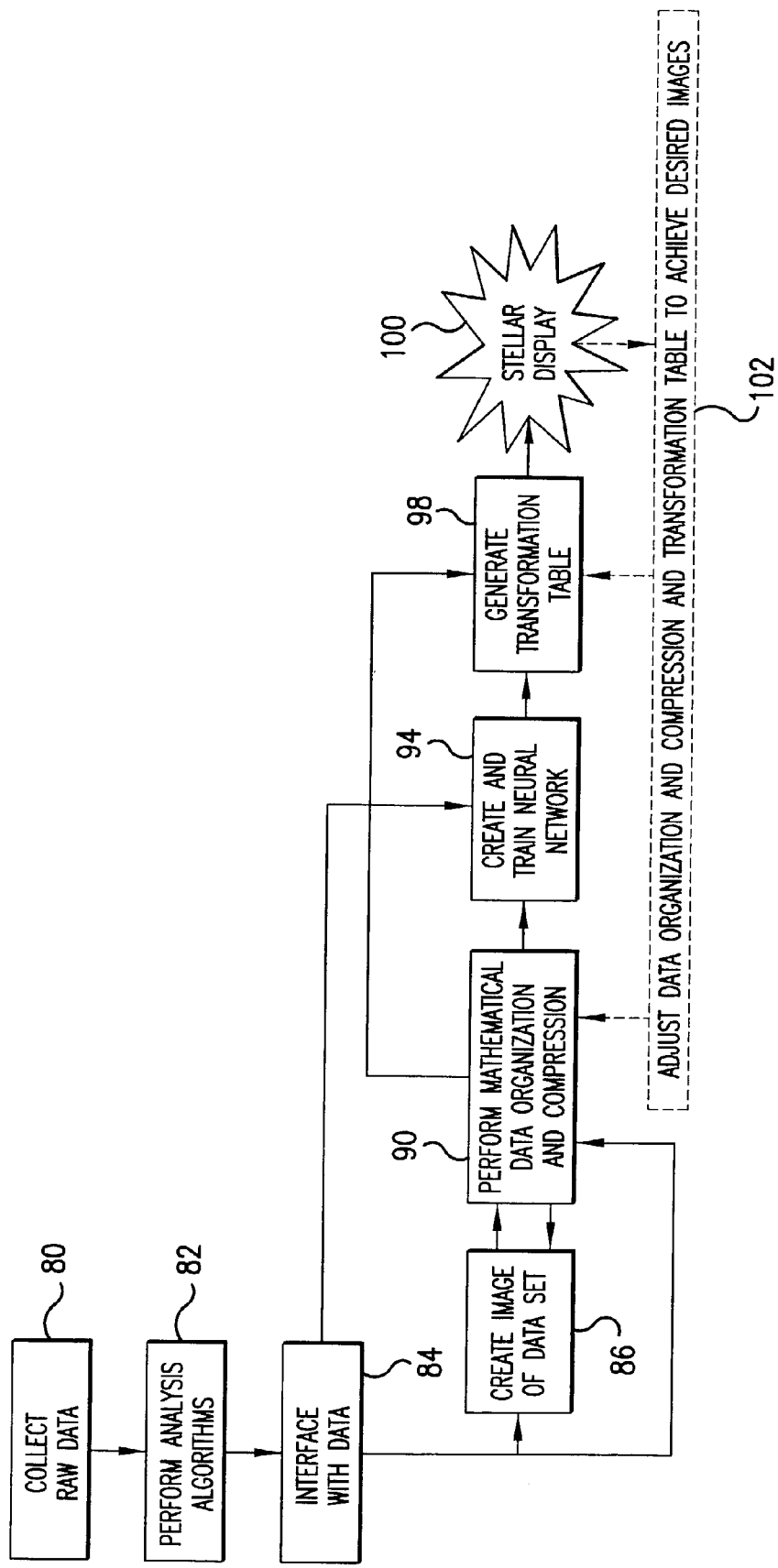
FIG. 7 depicts the method of creating the stellar icon of FIG. 3 of the invention.

FIG. 7 depicts the operation of the system of FIG. 6 to create the stellar icon 20 for a sample that the user wishes to represent. In step 80, a laboratory instrument can generate the raw data. The data can then be transferred to the processor 40 by electronic communication such as a network or the Internet. Further, the data can be manually entered into the processor 40 using the keyboard 53 or transferred by inputting electronic media into the processor 40.

Figure 1:
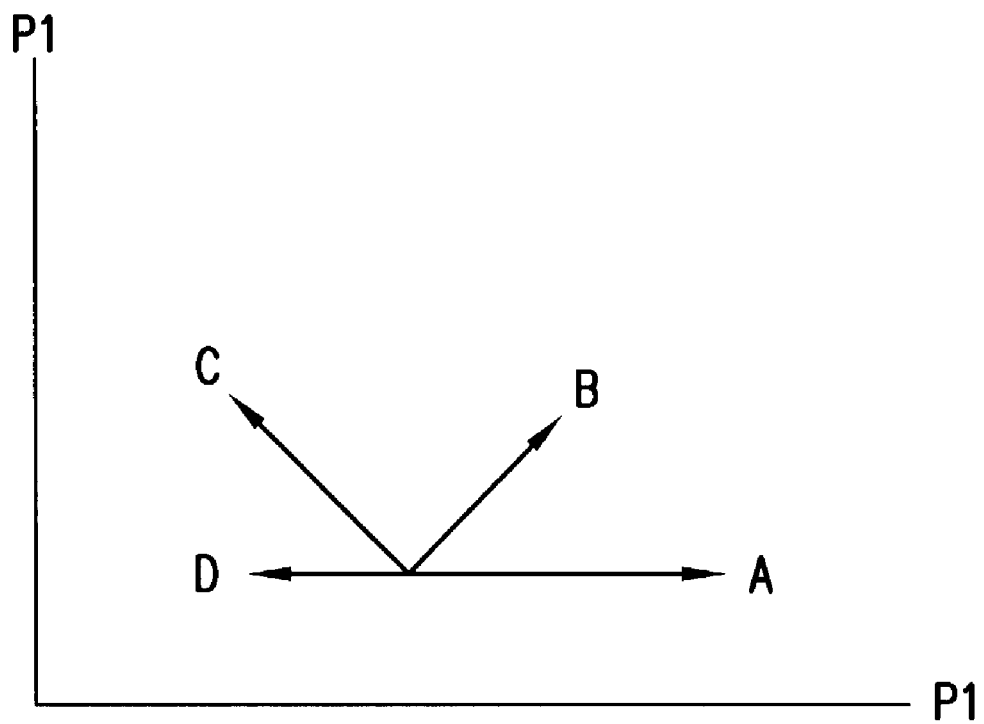
FIG. 1 depicts an example of a biplot of sample data.
Figure 2:
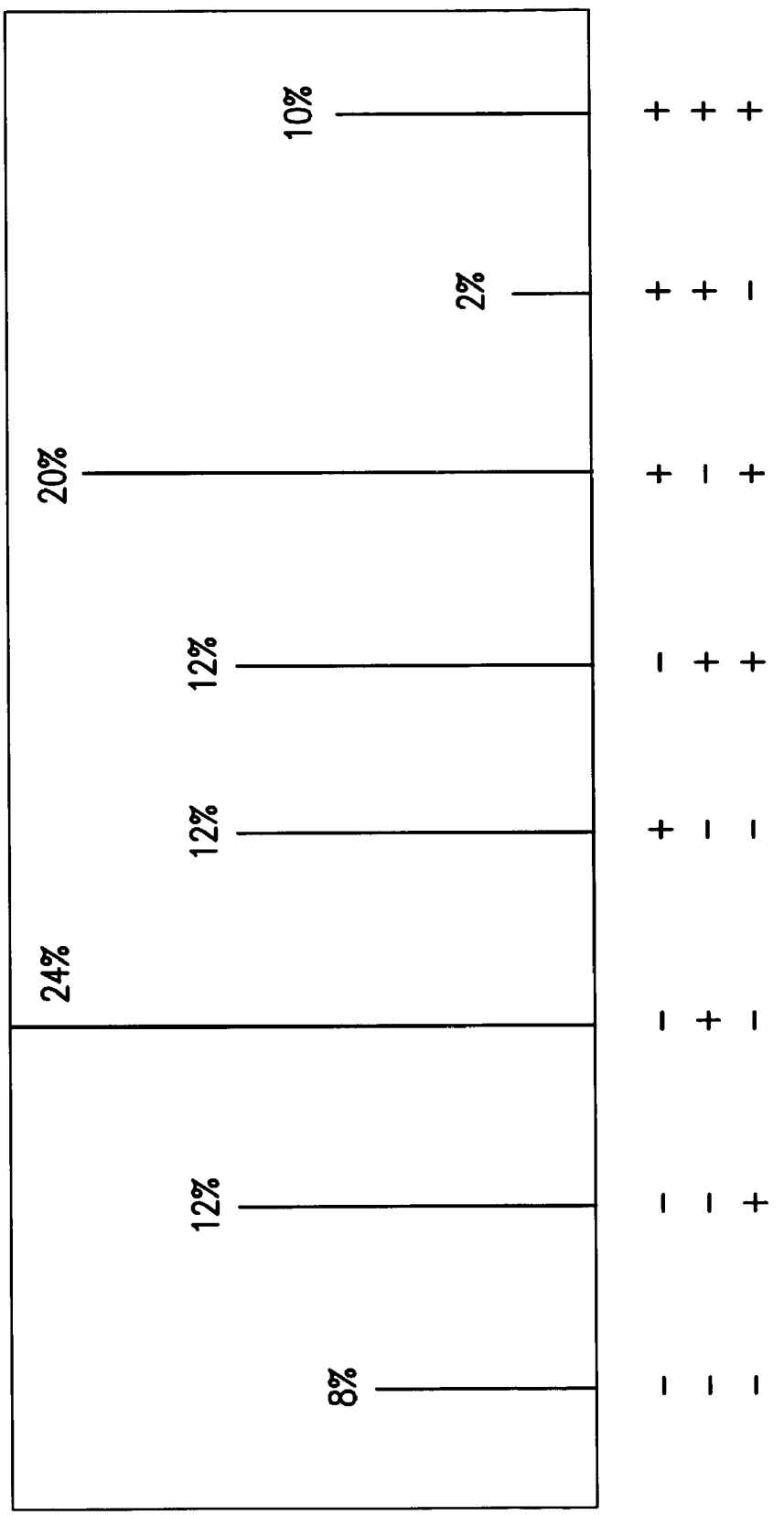
FIG. 2 depicts a prism representation of sample data.

In step 82, the raw data is input to the analysis algorithm. As is known in the art, analysis algorithms determine the data's constituents and their associated attributes. Similar to the analysis that was used to create the prism of FIG. 2, the analysis algorithms can designate each sample data entry as either positive or negative according to whether or not the attribute is present in the sample within the predetermined range.

In step 84, double-checking of the results of the analysis section 41 can occur by user interface. The processor 40 can display the analysis results on monitor 33. If the research is occurring in a university laboratory, the researcher can check to ensure the analysis algorithms are operating properly. If the sample is being analyzed to determine the health status of an individual, a doctor or laboratory technician can perform the double-checking of the results. If it appears to the user that the results of the analysis are incorrect, then the user can change the analysis criteria to achieve correct results. The changes can be made by using the keyboard 53 or mouse 55 to interface with the processor 40 and analysis section 41 to correct the results.

In step 86, the data from the analysis section 41 is transferred to the data converting section 43. In a preferred embodiment, the data converting section 43, converts the data from the input format to gray scale or other pseudo color image. For example, if the input data includes a concentration for various constituents in the input spreadsheet, the concentrations will be identified by shading scaled from 0–255 for a black and white image. The gray scale image can be used to visualize the data organization and compression process. In addition, the resulting gray scale image can provide a pictorial view of the relative variance within the database to visually analyze a particular component of the test sample compared to the database of samples.

In step 90, the data organization and compression section 45 transforms the data to determine the most significant variance and co-variance relationships using mathematical processing by methods that are known to those skilled in the art, such as Principal Components Analysis, Fourier Transform or Wavelet Transformations. These relationships are utilized to identify the constituents and their relevance on the icon. The identification of the most critical constituents is utilized to optimize the stellar display.

In step 94, the training of the neural network 60 is performed on the basis of the reference information and the results of the data organization and compression 90. The neural network 60 can be provided with the analyzed data from the data organization and compression section 45 and reference data, which can be provided from a source other than the data organization and compression section to establish the icon to be used. More specifically, multiple patients can have the same disease, which would be indicated by a particular icon, but the specific values of the attributes would be dependent on the specific test specimen. For example, the neural network 60 instructs the transformation table 47 as to which stellar icon is appropriate.

Moreover, if the neural network 60 determines that a significant portion of the samples have four T-cell receptor sites per white blood cell, then the neural network can generate a rule that designates those samples having four receptor sites per white blood cell as normal and this icon definition transferred to the transformation table 47.

In step 98, the transformation table combines the stellar icon selection received from the neural network 60 with the sample data to create the instructions for the icon generator 49 to create the icon. The transformation table 47 functions to identify the attributes and/or constituents that are to be displayed in the resulting stellar icon based upon the output of the neural network 60. In addition, the transformation table contains the visual representation factors of the finger portion 25 of the stellar icon, such as the finger position on the base portion, the length of the finger portion 25, the width of the finger portion, and color of the finger portion 25. The transformation table utilizes the information relating to a particular sample derived from the data organization and compression section 45 in conjunction with the visual representation factors to develop the stellar display definition and passes this information to the icon generator 49.

In step 100, the icon generator 49 receives the display definition from the transformation table 47 and creates the graphical display information. This information is then passed to the output device in conjunction with the OLE section 48 instructions to the output device for presentation. The stellar icon is thereby created.

Optionally, step 102 allows users, such as those described in step 84, to manually adjust the transformation table 47 or results of the analysis algorithm 82.

Figure 8:
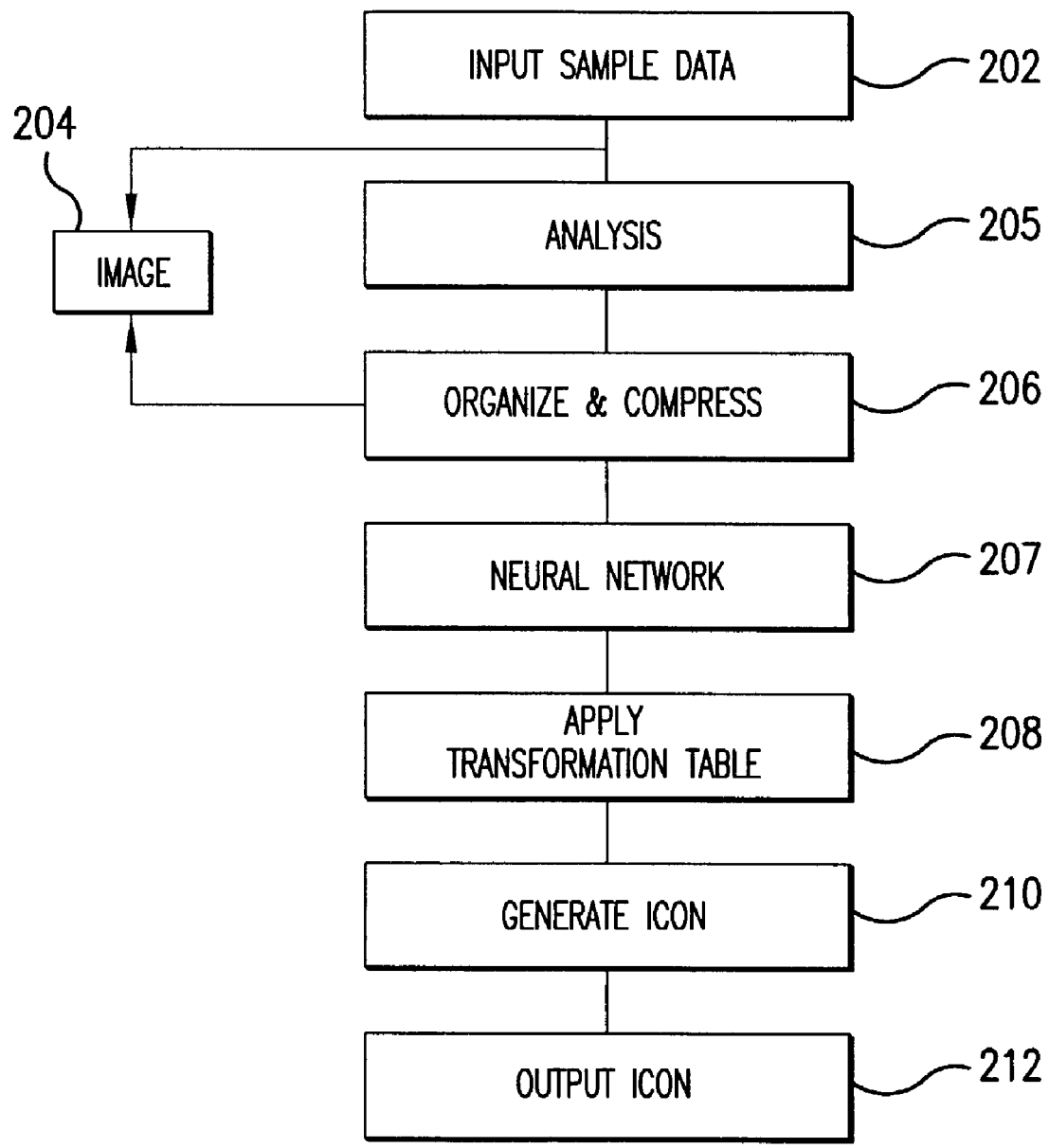
FIG. 8 depicts a method of creating the stellar icon for each new patient sample and associating values of the fingers of the stellar icon with constituents determined from analysis of the patient sample.

As shown in FIG. 8, a stellar icon can be formed to represent attributes of a constituent of a single sample or a pool of samples. For example, a doctor can order the analysis of a blood sample to determine if a patient is healthy or not. The neural network 60 and transformation table 47 are already formed as discussed above with reference to FIG. 7. Once the patient's data is collected in step 202, the data is converted to an image in step 204, and analyzed in the analysis section in step 205, and transferred to the data organization and compression section 45 in step 206. The image created in step 204 can also be used in step 206 to visualize the data organization and compression process.

In FIG. 8, the neural network step 207 uses the results of the data organization and compression analysis 206 to analyze the data and select the applicable stellar icon. In step 208, the transformation table 47 determines how to represent the data in the form of the stellar icon. For example, the transformation table designates whether or not the corresponding finger portion 25 should be on the upper hemisphere 27 or lower hemisphere 29 of the base portion 23. Further, the transformation table designates how long to make the finger portion 25 and the relative position on the base portion 23 of the finger portion 25.

From the information received from step 208, the next step 210, generates the icon to send to the output device as shown in step 212. Finally, in step 212, the icon 20 is output.

EXAMPLE 1

Utilization of Iconized Display for Identification of Acute Myelogenous Leukemia Sample A test sample is allocated into several tubes each having multiple monoclonal antibodies known to those skilled in the art to have relevant clinical indications of normalcy and abnormalcy. The tubes are then processed by an instrument, such as flow cytometer, to enumerate the constituent cells present in the sample and their attributes, which in the present case comprises relative intensity of light scatter or fluorescence intensity of each constituent.

This data is then input to the analysis section 41 wherein specific analysis strategies, such as gating, are employed to eliminate interference, such as caused by debris in the sample which can affect the analysis of the data. The analyzed data is transferred to the data organization and compression section 45 wherein the attributes of the constituents are compared to the attributes of the previous database. The organized data is then transferred to the neural network 60 which determines which category the sample data fits, which in this case is determined to be representative of acute myelogenous leukemia.

This category designation is then transferred to the transformation table 47. An acute myelogenous leukemia designates a path through the transformation table, which accumulates the specific factors for the stellar display. These factors are then applied to the sample data and the definition of the stellar display is then completed. The definition is then transferred to the icon generator 49, which completes the graphical creation of the icon. This is then sent to the output device 30, such as a monitor, with instructions from the OLE 48 to display the icon for the user.

An icon is generated according to FIG. 9 which shows positive constituents on the upper hemisphere CD3+ with an attribute of 10%; and negative constituents on the lower hemisphere comprised of CD34+CD13+ and CD33+ with an attribute of 55%; and an additional negative constituent of HLADR+CD34+ with an attribute of 35%. This indicates to the clinician that the test sample is an abnormal sample indicating Acute Myelogenous Leukemia.

The invention being thus described, it will be obvious that the same can be varied in many ways. Such variations are not to be regarded as a departure from the spirit and scope of the invention, and all such modifications as would be obvious to one skilled in the art are intended to be included within the scope of the following claims.

What is claimed:

1. A method of representing a plurality of constituents of a sample, the method comprising the steps of:
    accessing a database of constituent attribute data,
    determining a range of expression for each attribute or plurality of attributes by analyzing the constituent attribute data in the database,
    determining an attribute expression for each attribute of each constituent of the sample or plurality of attributes of each constituent of the sample,
    determining if each attribute expression is within or equal to the determined range,
    designating the constituent as acceptable when the corresponding attribute expression is within the determined range and designating the constituent as unacceptable when expression is not within the determined range,
    generating an icon having a base member and a plurality of finger members such that each finger member of the plurality of finger members corresponds to at least one constituent of the sample and each finger member has a base and a length which are functions of an expression of at least one attribute of the corresponding constituent and such that the base member has a first portion and a second portion where the base of each finger member corresponding to a constituent designated as acceptable is positioned on the first portion of the base member and the base of each finger member corresponding to a constituent designated as unacceptable is positioned on the second portion of the base member, and
    displaying the icon.

2. The method of claim 1, further comprising the step of:
selecting constituents of a plurality of constituents of a sample to be represented.

3. The method of claim 1, further comprising the step of:
analyzing the sample to determine the attributes of a plurality of constituents in the sample.

4. The method of claim 2, wherein
the step of selecting the constituents includes selecting the constituents based on an importance or expression of each constituent.

5. The method of claim 4, wherein
the importance of each constituent is determined by an evaluation of a database of constituent attributes of a plurality of research samples.

6. The method of claim 2, wherein
the step of selecting the constituents includes using an artificial intelligence system to select the constituents based on the importance of each constituent as determined by the artificial intelligence system evaluation of a database of research samples.

7. The method of claim 1, further comprising:
applying a color or shading to the finger member such that a different color or shading represents each attribute of the plurality of constituents of the sample.

8. The method of claim 1, further comprising:
identifying an expression of an attribute by a position of the finger member on the base member including positioning a finger member with the highest expression of an acceptable attribute on a relatively highest position of the first portion of the base member and positioning the finger member with the highest expression of an unacceptable attribute on the relatively lowest point of the second portion of the base member.

9. The method of claim 1, wherein
the first portion is opposite the second portion.

10. The method of claim 1, wherein
the first portion is above the second portion.

11. The method of claim 1, wherein
the base member is circular, spherical, oval, polygonal or any three dimension configuration.

12. The method of claim 1, wherein
the step of displaying the icon includes printing the icon or displaying the icon on a monitor.

13. The method of claim 1, wherein the sample is a blood, chemical or organic tissue sample.

14. The method of claim 1, wherein each finger member of the plurality of finger members corresponds to a plurality of constituents of the sample.

15. The method of claim 1, wherein the icon is multidimensional.

16. The method of claim 1, wherein the step of designating each constituent includes designating each constituent as being acceptable or unacceptable as a function of the expression of a plurality of attributes of the constituent.

17. The method of claim 1, further comprising: performing data organization and compression to identify constituents and attributes to be represented based on a degree of variance.

18. A method of representing medical data samples, the method comprising:
accessing a database of constituent attribute data for the medical samples,
determining a range of expression for each attribute or plurality of attributes by analyzing the constituent attribute data in the database,
determining an attribute expression for each attribute of each constituent of the sample or plurality of attributes of each constituent of the sample,
determining if each attribute expression is within or equal to the determined range,
designating the constituent as acceptable when the corresponding attribute expression is within the determined range and designating the constituent as unacceptable when expression is not within the determined range,
generating an icon having a base member and a plurality of finger members such that each finger member of the plurality of finger members corresponds to at least one constituent of the medical samples and each finger member has a base and a length which are functions of an expression of at least one attribute of the corresponding constituent and such that the base member has a first portion and a second portion where the base of each finger member corresponding to a constituent designated as acceptable is positioned on the first portion of the base member and the base of each finger member corresponding to a constituent designated as unacceptable is positioned on the second portion of the base member, and
displaying the icon.

19. The method of claim 18, further comprising the step of:
selecting constituents of a plurality of constituents of a medical sample to be represented.

20. The method of claim 1, wherein the base and finger members are user-selectable such that selection of the base member by a user actuates a processor to display information about the sample and selection of a finger member by the user actuates a processor to display the constituent attribute data.

* * * * *